(12) United States Patent
Hoffman et al.

(10) Patent No.: US 7,729,865 B2
(45) Date of Patent: Jun. 1, 2010

(54) COMPUTERIZED METHOD AND SYSTEM FOR AUTOMATED CORRELATION OF GENETIC TEST RESULTS

(75) Inventors: Mark A. Hoffman, Lees Summit, MO (US); Ginger H. Kuhns, Liberty, MO (US); Kevin M. Power, Pleasant Valley, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 842 days.

(21) Appl. No.: 10/886,335

(22) Filed: Jul. 7, 2004

(65) Prior Publication Data

US 2005/0074795 A1 Apr. 7, 2005

Related U.S. Application Data

(60) Provisional application No. 60/509,006, filed on Oct. 6, 2003.

(51) Int. Cl.
*G06F 7/00* (2006.01)

(52) U.S. Cl. ............................ 702/19; 702/20; 703/11; 707/102; 435/6; 436/501

(58) Field of Classification Search .................. 702/19, 702/20; 703/11; 707/102; 435/6; 436/501
See application file for complete search history.

(56) References Cited

U.S. PATENT DOCUMENTS

| | | | | |
|---|---|---|---|---|
| 5,631,844 | A * | 5/1997 | Margrey et al. | ............... 702/22 |
| 6,317,700 | B1 * | 11/2001 | Bagne | ...................... 702/181 |
| 7,529,685 | B2 * | 5/2009 | Davies et al. | .................. 705/3 |
| 2003/0040002 | A1 * | 2/2003 | Ledley | ......................... 435/6 |
| 2003/0082544 | A1 * | 5/2003 | Fors et al. | ...................... 435/6 |

* cited by examiner

*Primary Examiner*—Mark K Zeman
(74) *Attorney, Agent, or Firm*—Shook, Hardy & Bacon L.L.P.

(57) ABSTRACT

The present invention relates to a method and system for automated correlation of genetic test results. The method includes: receiving a first genetic test result from an individual's genetic history and receiving a second genetic test result for the individual. The method further includes determining based on result criteria if the second genetic test result should be identified as the primary genetic test result for the individual and, if so, identifying said second genetic test result as the primary genetic test result in the individual's genetic history.

15 Claims, 5 Drawing Sheets

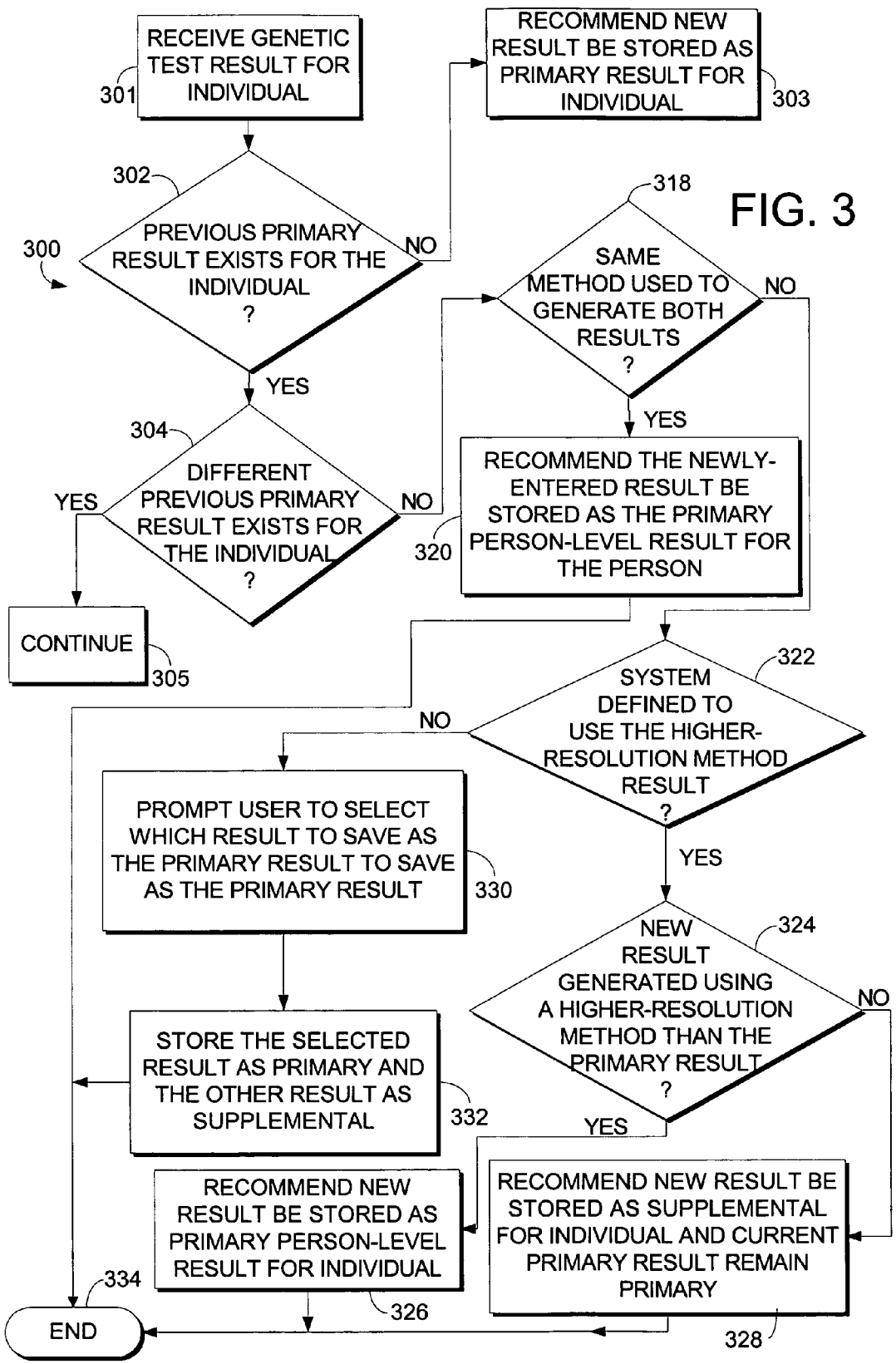

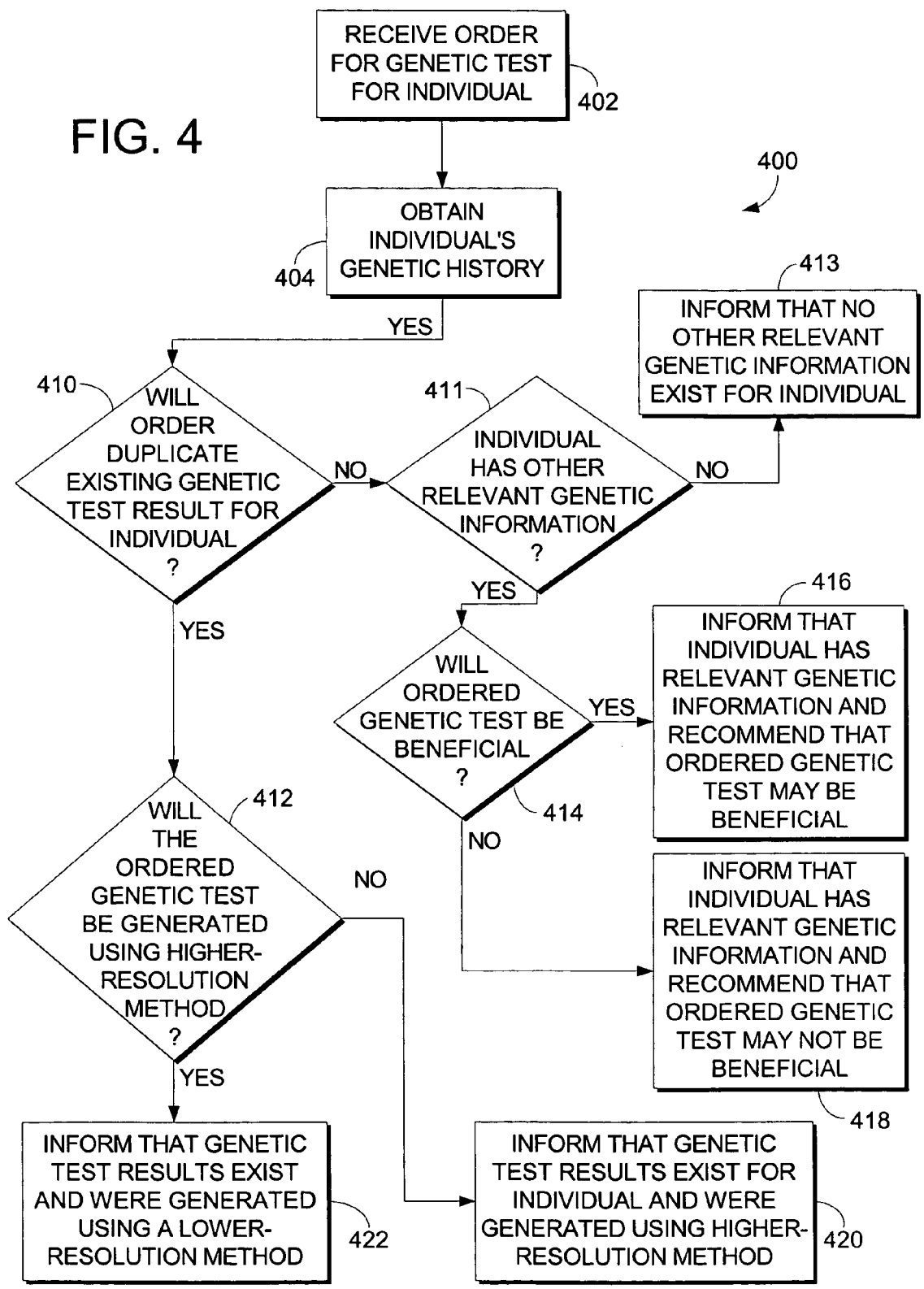

333# COMPUTERIZED METHOD AND SYSTEM FOR AUTOMATED CORRELATION OF GENETIC TEST RESULTS

CROSS-REFERENCE TO RELATED APPLICATIONS

This application claims the benefit of priority of U.S. Provisional Application No. 60/509,006 filed on Oct. 6, 2003.

STATEMENT REGARDING FEDERALLY SPONSORED RESEARCH OR DEVELOPMENT

Not applicable.

TECHNICAL FIELD

The present invention relates generally to the field of computer software. More particularly, the invention relates to a method and system for automated correlation of genetic test results.

BACKGROUND OF THE INVENTION

Unlike many patient test results in a health care environment, genetic test results generally have life-long value. Current clinical information systems are not able to automatically recognize discrepant or duplicate genetic test results generated at any point in an individual's clinical care. Current clinical heath care information systems also cannot appropriately reconcile discrepant or duplicate genetic test results.

As genetic testing becomes more prevalent, tools and methods to ensure quality and accuracy of genetic test results stored in electronic records will become increasingly necessary. A method and system for automatically correlating and comparing genetic test result values for individuals would be beneficial.

SUMMARY OF THE INVENTION

In one embodiment of the present invention, the invention relates to a method for automatically determining the primary genetic test result for an individual. The method receives a first genetic test result from an individual's genetic history. The first result is identified as a primary genetic test result for the individual. The method receives a second genetic test result for the individual. Based on at least one result criterion, the method determines if the second genetic test result should be identified as the primary genetic test result for the individual and, if so, identifies the second result for said primary genetic test result in the individual's genetic history.

In yet another embodiment of the present invention, a method for automatically correlating genetic test results for an individual based on the method employed to determine first and second genetic test results is shown. The method receives a first genetic test result from an individual's genetic history, the first result is identified as a primary genetic test result for the individual. The method receives a second genetic test result for the individual and identifies a method employed to determine the first and second genetic test results. The method determines if the technique employed to determine the second genetic test result is superior to the method employed to determine the first genetic test result and, if so, identifies the second genetic test result as the primary genetic test result in the individual's genetic history.

In still another embodiment of the present invention, a system for automatically determining the primary genetic test result for an individual is shown. The system includes a first receiving module for receiving a first genetic test result from an individual's genetic history, the first result is identified as a primary genetic test result for the individual and a second receiving module for receiving a second genetic test result for the individual. The system further includes a determining module for determining based on the at least one result criterion if the second genetic test result should be identified as the primary genetic test result for the individual. If so, the system identifies the second result as said primary genetic test result in the individual's genetic history.

In yet another embodiment, a method for determining whether an ordered genetic test will duplicate at least one existing genetic test result for an individual is described. The method receives an ordered genetic test for an individual, where the genetic test is for a particular genetic sequence or variant thereof. The method determines whether the individual has at least one existing genetic test result for the particular genetic sequence or variant thereof; and if so, provides notice of the at least one existing genetic test result for the individual.

BRIEF DESCRIPTION OF THE DRAWING

The present invention is described in detail below with reference to the attached drawing figure, wherein:

FIG. 3 is a flow diagram of a method for correlating genetic test result values based on method used to generate the genetic test results in accordance with an embodiment of the present invention; and FIG. 4 is a flow diagram of a method for providing notice as to whether relevant genetic results exist for an individual in accordance with an embodiment of the present invention.

DETAILED DESCRIPTION OF THE INVENTION

The present invention provides a system and method for automatically correlating genetic test results or orders for genetic testing. The system and method of the present invention allows genetic test results to be used throughout a person's life rather than for one or more specific encounters. The system and method of the present invention automatically determines whether a new genetic test result value received by the system duplicates an existing result, disagrees with an existing result and/or extends an existing result when a new technique is applied. The invention also allows inbound orders for genetic tests to be evaluated against historic orders to determine if there is redundancy and to allow the user to determine whether to proceed with the order.

Figure 1A:
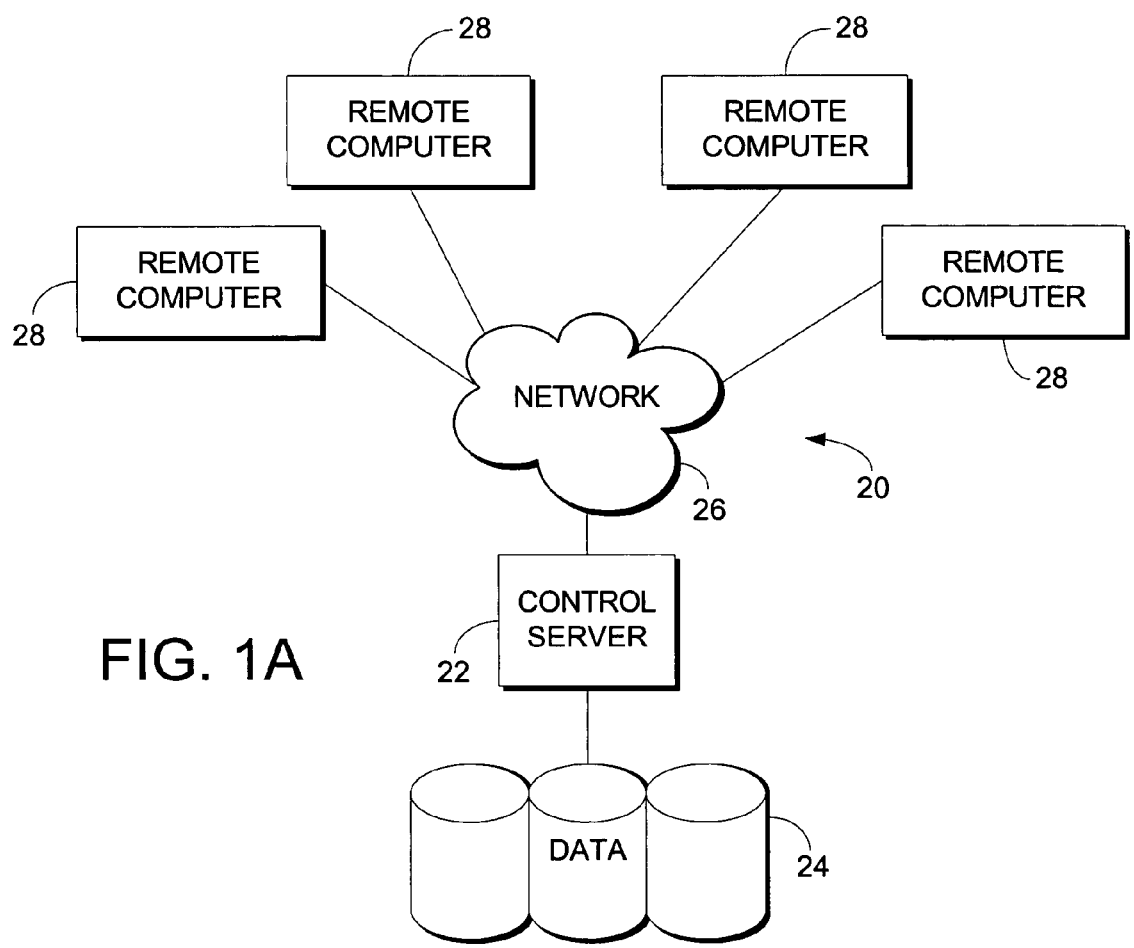
FIG. 1A is a block diagram of a computing system environment suitable for use in implementing the present invention.

With reference to FIG. 1A, an exemplary medical information system for implementing the invention includes a general purpose-computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and non-removable media. By way of example, and not limitation, computer readable media may comprise computer storage media and communication media. Computer storage media includes both volatile and nonvolatile, removable and non-removable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1A, provide storage of computer readable instructions, data structures, program modules, and other data for server 22.

Server 22 may operate in a computer network 26 using logical connections to one or more remote computers 28. Remote computers 28 can be located at a variety of locations in a medical or research environment, for example, but not limited to, clinical laboratories, hospitals, other inpatient settings, a clinician's office, ambulatory settings, medical billing and financial offices, hospital administration, veterinary environment and home health care environment. Clinicians include, but are not limited to, the treating physician, specialists such as surgeons, radiologists and cardiologists, emergency medical technicians, physician's assistants, nurse practitioners, nurses, nurse's aides, pharmacists, dieticians, microbiologists, laboratory experts, genetic counselors, researchers, veterinarians and the like. The remote computers may also be physically located in non-traditional medical care environments so that the entire health care community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, satellite dish, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

Although the method and system are described as being implemented in a WINDOWS operating system operating in conjunction with an Internet-based system, one skilled in the art would recognize that the method and system can be implemented in any system supporting the receipt and processing of genetic test results. As contemplated by the language above, the method and system of the present invention may be implemented on a stand-alone desktop, personal computer or any other computing medical environment, solitary research lab or any of a number of other locations.

Figure 1B:
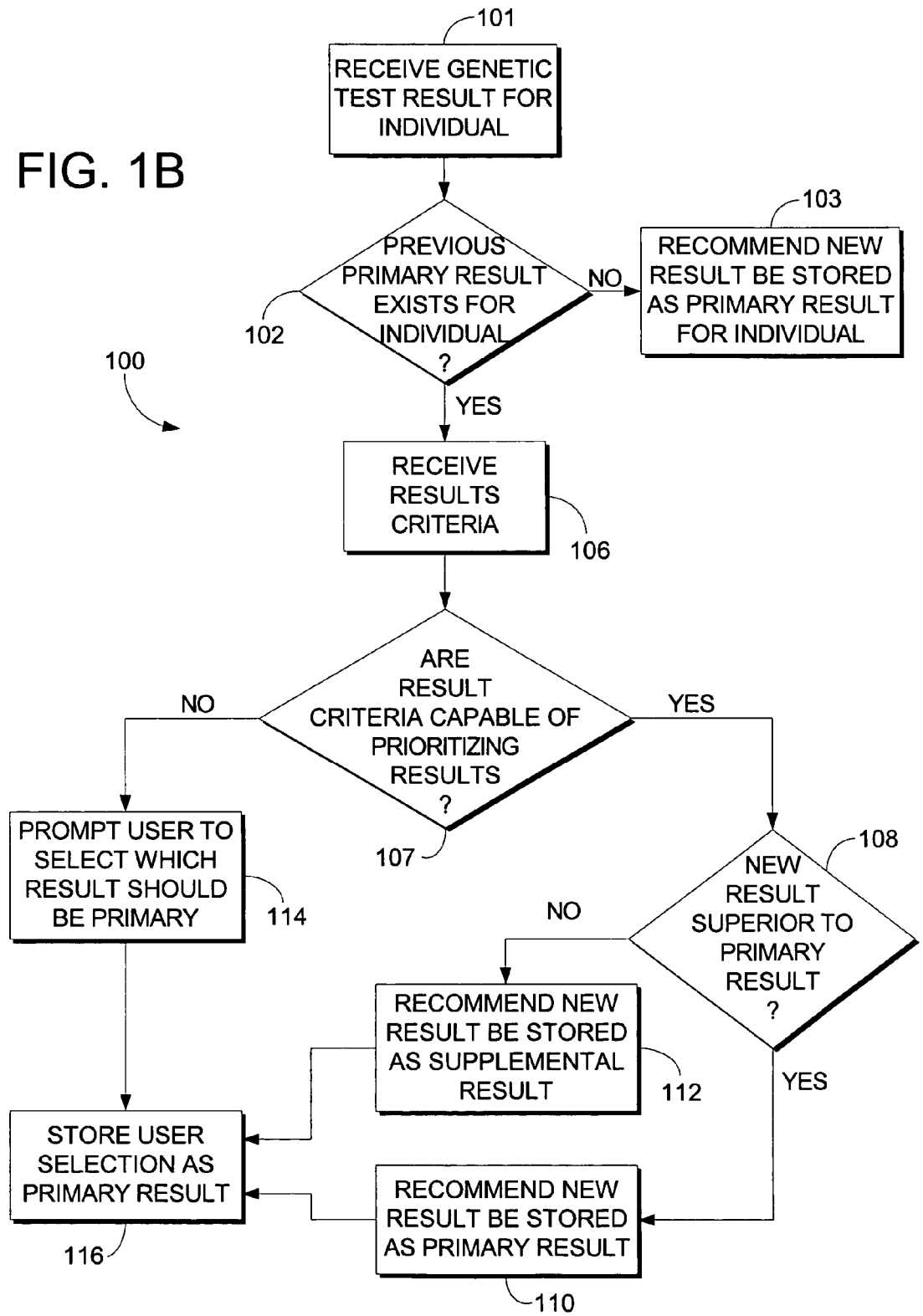
FIG. 1B is a flow diagram of a method and system for automatically correlating genetic test result values in accordance with an embodiment of the present invention.

With reference to FIG. 1B, a method of automatically correlating genetic test result values 100 is provided. At block 101, the system receives a genetic test result for an individual. The system of the present invention retrieves genetic test results for an individual from an application or module in a healthcare information technology (HCIT) system. Alternatively, the system may receive a genetic test results directly from a user.

At block 102, the system queries the data structure (e.g., database) to determine whether compatible genetic test results exist for the individual. Compatibility can be determined by: matching identifiers from a controlled vocabulary, string matching or application of a semantic network that organizes genomic information. For example, if the genetic test result for the individual is a specific mutation in the gene that causes cystic fibrosis, the system queries to determine if the individual has pre-existing genetic test results for any versions of the cystic fibrosis gene or any cytogenetic observations that would include the cystic fibrosis gene. If, at block 102, the system determines that the individual does not have pre-existing genetic test results in the database, the system recommends that the new genetic test result be identified and stored as the primary genetic test result for the individual at block 103. Alternatively, the system automatically identifies and stores in a database, table and/or the individual's electronic medical record the new genetic test result as the primary result for the individual. The primary result is the persistent value for a specific genetic result for an individual. The genetic test result stored as the primary result is given priority when the genetic data is used such as in a healthcare information technology system (e.g., in a decision support rule, presentation to the clinician, etc.). Supplemental genetic test results may be stored with equal value to one another or may be ranked relative to one another.

If, at block 102, the system determines the individual has a pre-existing primary genetic test result for the particular gene, the system obtains or receives the pre-existing genetic test result for the individual. The system proceeds to block 106 and receives result criteria. In one embodiment, the system queries a data structure (e.g. database or external reference table) for the result criteria to be applied. At block 107 the system determines whether the result criteria are capable of prioritizing results. If at decision block 107 the system determines that the result criteria are capable of prioritizing results, the system proceeds to block 108.

Some of the result criteria that can be applied to determine which genetic test result should be the primary genetic test result include: the technique employed to obtain the genetic test result, information regarding the user performing the genetic test, such as user qualifications, the most recent genetic test result, instrument maintenance status, status of controls, statistical probabilities, attributes of the original sample and combinations thereof.

Degrees of certainty can be assigned to the techniques that are used to generate results. Based on a ranked list of available techniques, the system can automatically make the primary result the result that was generated by the highest confidence technique. Among the factors that can be included in the ranked listing of results are quality measures associated with various instruments. The resolution of a molecular diagnostic test or technique refers to the accuracy and reliability of test. For example, DNA sequencing to determine if a nucleotide replacement has occurred at a specific position may be defined as a higher-resolution technique than running polymerase chain reaction (PCR) with a specific probe for the polymorphism mutation.

Some current techniques for identifying a human mutation, including genetic test results, are listed in the following order beginning with the highest quality: DNA sequencing, Restriction Fragment Length Polymorphism (RFLP) and Allele specific PCR. For example if an existing result is generated by RFLP and the new result is generated by DNA sequencing, the system will determine that the new result was generated by a higher confidence technique and in turn the new result is promoted to be the primary result for the individual. If the new result had been generated by Allele specific PCR, the existing result generated by RFLP would have remained as the primary result because in this example RFLP is considered to be a higher confidence technique. One of skill in the art will appreciate that the techniques may be ranked in varying order depending on the outcomes generated by each result and the order of confidence may vary. Further, new techniques may also be developed and added to the list of techniques for generating genetic test results.

In systems that store credentials, years of experience, training status, personnel test scores or other means that can be used to consistently evaluate the likely qualifications of the person performing the test, this information may be used as a result criterion to be applied to select a primary result. The most recent result may also be used as a result criterion such that the most recent result is stored as the primary by default. The system may be configured to provide a time window during which this criterion may be applied. for example result criterion regarding user qualifications will only be applied to results that were performed more than a week apart.

In systems where the maintenance of a device or instrument is logged into the system, the status of the devices relative to one another may be used as a result criterion. For example, the result from the most recently maintained device is identified as being primary result. In one embodiment, this result criterion is applied when the same technique is applied to generate conflicting results. Another result criterion is the status of controls. For example, if either one result was associated with a batch that included either a failed positive control or a failed negative control and the other result is associated with successful controls, the result with successful controls would be identified as the primary result.

Another result criteria that may be applied is the likelihood that one result is more accurate than the other. For example, if one result is statistically more probable than the other, based on factors such as known population genetics, then the result with the greatest statistical likelihood would be identified as the primary result.

Additionally, the attributes of the original sample may be used as a result criterion. If, for example, quantifiable attributes, such as purity or a specimen grading scale, are associated with information about the original sample, these attributes can be used to determine which result should be identified as the primary result.

Each of the result criterion may be applied individually, collectively or in a cascading manner as may be pre-defined in the system. A collective use of result criteria may include a combinatorial rating in which values from each result criteria are combined to determine which genetic test result should be primary. A cascading approach would involve relative ranking of the result criterion. Lower ranked result criteria would only be used when higher ranked result criteria fail to make a recommendation. For example, if two genetic test results generated by the same technique disagree, the user qualification result criterion is applied.

With reference to FIG. 1B, at decision block 106, it is determined whether the system is defined to use result criteria to determine whether the newly received genetic test result or the pre-existing primary genetic test result should be stored as the primary genetic test result for the individual. If so, the system proceeds to decision block 108 and determines whether the new result is superior to the existing primary result by applying result criteria.

At block 108, if the system determines that the new result is superior to the existing primary result based on the result criteria, the system recommends to the user that the new result be stored as the primary genetic test result for the individual at block 110. However, at block 108, if the system determines that the new result is not superior to the existing primary result, the system recommends to the user that the new result be stored as a supplemental genetic test result for the person and the existing primary genetic test result remain the primary genetic test result at block 112. The system receives the user's selection of which result to store as the primary result for the individual. The system provides a recommendation to a user so that based on the recommendation and the user's knowledge and training, the user can select which result should be stored as the primary result. At block 116, the system stores the user's selection as the primary result. Alternatively, the system automatically stores either the new result or the existing primary result without making a recommendation to the user.

Returning to decision block 106, if the system is not configured to use result criteria to determine whether the newly received genetic test result or the pre-existing primary genetic test result should be stored as the primary genetic test result for the individual, the system prompts the user to select which result to save as the primary result at block 114. At block 116, the system stores the selected result as the primary genetic test result for the individual and the other result as the supplemental genetic test result. In another embodiment, the user is given the opportunity to determine which of the results is given primary status in the system using their training and knowledge in combination with the recommendation of the system.

Figure 2:
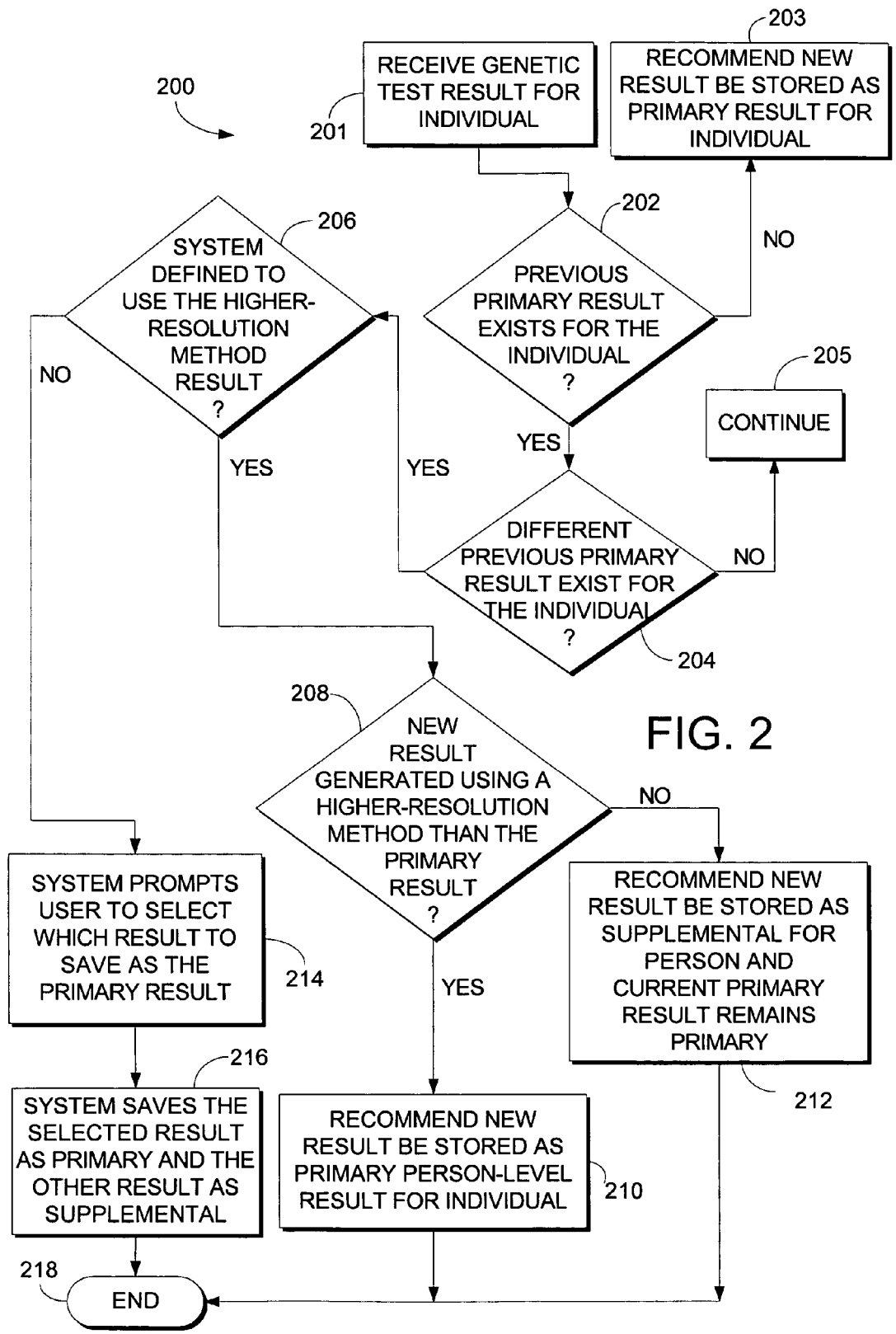
FIG. 2 is a flow diagram of a method for correlating genetic test result values based on method used to generate the genetic test results in accordance with an embodiment of the present invention.

With reference to FIG. 2, a method of automatically correlating genetic test result values 200 based on resolution technique used result criteria is provided. At block 201, the system receives a genetic test result for an individual. Again, the genetic test result may be for any organism and may be entered by a user or transmitted from another system.

At block 202, the system queries the data structure (such as a database and/or the individual's electronic medical record) to determine whether a genetic test result exists for an individual for the genetic test result received. For example, if the genetic test results received for the individual is a specific mutation or polymorphism of the gene known to cause Alzheimer's, the system queries to determine if the individual has pre-existing genetic test results for any versions of the Alzheimer's gene or cytogenetic observations that include the Alzheimer's gene. If, at block 203, the system determines that the individual does not have pre-existing genetic test results for the particular gene in the database, the system stores the new genetic test result as the primary result for the individual for the particular gene at block 203.

If, at block 202, the system determines the individual has a pre-existing genetic test result for the individual, the system obtains the pre-existing genetic test result for the individual and compares the newly received genetic test result with the existing genetic test result at block 204 to determine if the new genetic test result is different from the primary genetic test result that exists for the individual. If the new genetic test result and the existing primary genetic test result are the same, the system continues at block 205. If the new genetic test result and the existing primary genetic test result are different and if the techniques used to obtain the results are provided in the system, the system determines whether the system is defined to store the test result using the higher-resolution technique result as the primary genetic test result for the individual at block 206. If the system is configured to store the result using the higher-resolution molecular diagnostic test as the primary genetic test results at block 206, the system proceeds to block 208.

At block 208, the system determines whether the new result was generated using a higher-resolution technique than the existing primary result. The resolution of a molecular diagnostic test or technique refers to the accuracy and reliability of test. For example, DNA sequencing to determine if a nucleotide replacement has occurred at a specific position may be defined as a higher-resolution technique than running polymerase chain reaction (PCR) with a specific probe for the polymorphism mutation.

At block 208, if the system determines that the new result was generated using a higher-resolution technique than was used to generate the existing primary result, the system recommends the new result be stored as the primary genetic test result for the individual for the particular gene at block 210. However, at block 208, if the system determines that the new result was generated using a lower-resolution technique than was used to generate the existing primary result, the system recommends the new result be stored as a supplemental genetic test result for the person and the existing primary genetic test result remains the primary genetic test result at block 212.

Returning to decision block 206, if the system is not configured to store the result generated by using the higher-resolution technique by default, the system prompts the user to select which result to save as the primary result at block 214. At block 216, the system stores the selected result as the primary genetic test result for the individual and the other result as the supplemental genetic test result. In this embodiment, the user is given the opportunity to determine which of the results is given primary status based on a recommendation from the system and the training and knowledge of the user.

With reference to FIG. 3, a method of automatically correlating genetic test result values 300 based on result criteria regarding resolution method used is provided. At block 301, the system receives a genetic test result for an individual.

At block 302, the system determines the individual has a pre-existing genetic test result for the individual. If not, the system recommends that the new result be stored as the primary result. If so, the system obtains the pre-existing genetic test result for the individual and compares the newly received genetic test result with the existing genetic test result at block 304 to determine if the new genetic test result is different from the primary genetic test result that exists for the individual.

If at decision block 304, if the system determines that the genetic test results are different, the system continues at block 305. If at block 304 the system determines the results are the same, the system proceeds to decision block 318. At block 318, the system determines whether the new genetic test result and the preexisting primary genetic test result were generated by the same technique. If, at block 218, the new genetic test result and the existing primary genetic test result were generated the same technique or the technique is unknown to the system, the system recommends to the user that the new genetic test result be stored as the primary genetic test result for the individual at block 320. The user can determine which result should be stored as the primary result based on the recommendation of the system and their knowledge and training. In an alternative embodiment, the system automatically stores the new genetic test result as the primary genetic test result for the individual without making any recommendations.

If at block 318, the same technique was not used to generate the new genetic test result and the preexisting primary genetic test result, the system proceeds to decision block 322. At block 322, the system determines whether it is defined to store the higher-resolution technique result by default. If the system is configured to store the result using the higher-resolution molecular diagnostic test as the primary genetic test results at block 322, the system proceeds to block 324.

At block 324, the system determines whether the new result was generated using a higher-resolution technique than the existing primary result. If at block 324, the system determines that the new result was generated using a higher-resolution technique than was used to generate the existing primary result, the system recommends the new result be stored as the primary genetic test result for the individual at block 326. However, if at block 324, the system determines that the new result was not generated using a higher-resolution technique than was used to generate the existing primary result, the system recommends the new result be stored as a supplemental genetic test result for the person and the existing primary genetic test result remains the primary genetic test result at block 328. The user can determine which result should be stored as the primary based on the recommendation of the system and the user's knowledge and training. Alternatively, the system automatically stores the primary result without making a recommendation.

Returning to decision block 322, if the system is not configured to store the result generated by using the higher-resolution technique by default, the system prompts the user to select which result to store as the primary result at block 330. The user may determine which result is assigned as the primary result based on the user's confidence in the quality of the sample submitted, confidence in the person or lab conducting the work, previous knowledge of the uncertainty with the result (i.e., whether the new result is known to be from a repeat test.) At block 332, the system stores the selected result as the primary genetic test result for the individual and the other result as the supplemental genetic test result. In another embodiment, a technique for informing or providing notice as to whether relevant genetic results exist for an individual is described in FIG. 4. At block 402, the system receives an order for a particular genetic test for an individual. An application or module in a healthcare information technology (HCIT) system transmits to the system of the present invention orders for genetic tests for an individual. Alternatively, the system may receive an order for a genetic test directly from a user. At block 404, the system obtains the relevant genetic history for the individual by querying a data structure. For example, relevant genetic results include actual genetic test results for the ordered genetic tests, cytogenetic results, and inferred genetic results based on population genetics or familial genetic history. The system proceeds to decision block 410 and determines if the ordered genetic test will duplicate one or more existing genetic test results for the individual. For example, an order for a genetic test for the cystic fibrosis gene will be duplicative if an existing genetic test result for the gene or any variants already exists for the individual.

If the individual does not have any actual genetic test results for the particular genetic sequences or variant thereof of the ordered genetic test at decision block 410, the system proceeds to 411. At block 411, the system determines if the individual has any other genetic information that is relevant to the genetic test being ordered. The other relevant genetic information includes cytogenetic observations, inferred results based on population genetics and family genetic information. One of skill in the art will appreciate that a variety of other relevant genetic information may also be included.

If the individual does not have any relevant genetic information the system informs or provides notice that relevant genetic information does not exist for the individual at block 413. If the individual has relevant genetic information relating to the particular genetic test being ordered at decision block 411, the system proceeds to block 414. At decision block 414 and determines whether the ordered genetic test will be beneficial based on the relevant genetic information. For example, if the relevant genetic results for the individual are cytogenetic results indicating that the individual is missing the chromosomal band where the cystic fibrosis gene is located, additional testing is unnecessary. If the genetic test ordered will not be beneficial at decision block 414, the system proceeds to block 418 and informs or provides notice of the relevant genetic information and that the ordered genetic test may not be beneficial. In one embodiment, notice is provided to a user.

If at decision block 414 the genetic test ordered will be beneficial, the system proceeds to block 416. Instances where genetic information is available but the genetic test ordered will still be beneficial include when the relevant genetic information is inferred genetic results based on population genetics of familial genetic history. At block 416, the system informs or provides notice that the individual has relevant genetic information and that the ordered genetic test may still be beneficial.

With reference again to decision block 410, if the order for the genetic test will duplicate an existing genetic test result for an individual the system proceeds to decision block 412. At decision block 412 the system queries the database for a ranking of techniques for identifying mutations and determines whether the ordered genetic test will be generated using a higher-resolution technique than the technique used to generate the existing genetic test result. As discussed above, some current techniques for identifying a human mutation, including genetic test results, are listed in the following order beginning with the highest quality: DNA sequencing, Restriction Fragment Length Polymorphism (RFLP) and Allele specific PCR. One of skill in the art will appreciate that the techniques may be ranked in varying order depending on the outcomes generated by each result and the order of confidence may vary and new techniques may also be developed and added to the list of techniques for generating genetic test results. For example, a DNA sequencing technique that will be used to generate the ordered genetic test will be a higher-resolution technique than a PCR technique used to generate the existing genetic test result. If at block 412, the ordered genetic test is generated using a higher-resolution technique, the system informs or provides notice at block 422 of the duplicative genetic test results and that the result was generated using a lower-resolution technique.

If at block 412 the ordered genetic test will not be generated using a higher-resolution technique, the system proceeds to block 420. At block 420 the system provides notice or informs of the duplicative genetic test result and that it was generated using a high-resolution technique. If the ordered genetic test will be generated using the same resolution technique, as the existing test result the system will provide notice that the duplicative genetic test result was generated by the same technique to be used by the ordered genetic test at bock 420. In one embodiment, after being provided notice at block 413, 416, 418, 420 or 422, a user will have an opportunity to continue or cancel the order based on the information and/or recommendations provided by the system. The technique of the embodiment described in FIG. 4 improves workflow, as the user does not need to request a review of prior genetic results each time they place an order. Furthermore, it prevents genetic tests from being performed when the may not be beneficial or appropriate given the individual's healthcare plan.

The present invention can be used with a semantic network describing biological relationships. The primary genetic finding would be linked to the specific DNA sequence, position, chromosome, genotype, and phenotype of an individual. For example, in a patient for whom an earlier result determined that an entire gene had been deleted, it could be appropriate to intercept orders or results for mutational analysis within the deleted gene. A semantic network would enable the system to make these complex associations.

One embodiment of the present invention utilizes a relational database to store individual results in a healthcare information system capable of performing a variety of tasks such as generating charges, managing an electronic medical record and other functions. Also included within the clinical information system is expert system capability to generate diverse responses to various user and system events. Alternative implementations of a relational database could include XML documents or an object oriented database integrated with a clinical information system. In the relational database system implementation, the system tracks the person demographics, person level results and the parameters that influence correlation events. The system of the present invention tracks the occurrence of the need for correlating genetic test results for an individual and the subsequent decisions made by the system and system users.

Tables 1-4 show an excerpt of exemplary fields and descriptions contemplated by the present invention to manage the information related to the aforementioned system and method.

TABLE 1

| Field | Description |
| --- | --- |
| PersonId | System generated identifier for a person. |
| PersonName | The person's name as entered by the registration system. |
| BirthDateTime | The person's birth date and time as entered by the registration system. |

TABLE 2

| Field | Description |
| --- | --- |
| ResultId | System generated identifier for a result. |
| PersonId | System generated identifier for a person. |
| ResultType | Indicate the type of result. |
| ResultValue | Stores the result value. |
| ResultDateTime | Date and time the result was entered. |
| ResultUserName | The unique id of the user who recorded this result. |
| PrimaryIndicator | Indicates if this result is the primary for this PersonId/ResultType combination. Any result not stored as primary would be considered supplemental. |
| ResultMethod | Stores the method that was used to generate the result value. |
| ResultMethodResolution | Stores the resolution of the ResultMethod. This could be used to rank the supplemental results. |

TABLE 3

| Field | Description |
| --- | --- |
| CorrelationEventId | System generated identifier for a correlation event. |
| CorrelationEventType | Indicates the type of correlation that occurred (IE, Different Primary Result or Different Method) |
| DecisionType | Indicates what the user choose to do with the correlation event. |
| CorrelationComment | Optional free text comment the user may enter during the correlation documentation. |
| CorrelationDateTime | Date and time the correlation event occurred |
| CorrelationUserName | The unique id of the user who responded to the correlation event. |
| PreviousResultId | The unique id of the existing primary result. |
| NewResultId | The unique id of the newly generated result. |

TABLE 4

| Field | Description |
| --- | --- |
| HigherResolutionIndicator | Indicates if the system should default a new result with a higher resolution as the primary result. |

Table 1 contains demographic information for the individual including, but not limited to, a system generated identifier of the individual, the individuals name and birth date. Table 2 contains information for storing individual genetic test results. The individual genetic test result information may include, but is not limited to, an identifier of the result, an identifier of the person, an identifier of the type of result, the genetic test result value, the date and time the result was entered, an identifier of the user who recorded the result, a primary indicator that indicates if the result is primary for the individual, the technique used to generate the result value and the resolution of the result technique (e.g., to rank supplemental results).

Table 3 contains correlation event information. Correlation event information includes a system generated identifier of the correlation event, the type of correlation that occurred (e.g., different primary result or different technique), the users decision regarding the correlation event, the data and time the correlation event occurred, an identifier of the user who responded to the correlation event, an identifier of existing primary genetic test results and an identifier of the new generated genetic test result. Table 4 contains information regarding correlation parameters for the method of the present invention. For example, the correlation parameters include a higher resolution indicator that indicates if the system should store a new genetic test result with a higher resolution as the primary genetic test result rather than the existing primary genetic test result for the individual.

In one embodiment, Tables 1-4 are combined into one relational database. One of skill in the art will realize that there are any number of ways for storing patient demographic information, individual genetic test result information, correlation event information and correlation parameters. One of skill in the art will also understand that genetic test results may be for any organism.

The present invention is a method and system for automatically correlating genetic test results for an individual. Although the invention has been described with reference to embodiments of the invention in the attached drawing figure, it is noted that substitutions may be made and equivalents employed herein without departing from the scope of the invention as recited in the claims. For example, additional steps may be added and steps omitted without departing from the scope of the invention.

We claim:

1. One or more computer storage media having computer-executable instructions embodied thereon for performing a method for automatically determining the primary genetic test result for an individual, the method comprising:

receiving a first genetic test result associated with the individual's genetic history, wherein the individual's genetic history is stored on one or more computer storage media associated with the individual's electronic medical record, said first genetic test result being identified as a primary genetic test result for the individual in the individual's electronic medical record;

receiving a second genetic test result for the individual;

determining a technique used to generate the first genetic test result and a technique used to generate the second genetic test result, each respective technique having a resolution associated therewith;

ranking the first and second genetic test results according to the resolution of each respective technique; and upon determining, based upon the ranking thereof, that the second genetic test result was generated by a technique with higher resolution, storing the second genetic test result as the primary genetic test result in association with the individual's genetic history in the electronic medical record;

upon determining, based upon the ranking thereof, that the second genetic test result was not generated by a technique with higher resolution, storing the first genetic test result as the primary genetic test result in association with the individual's genetic history in the electronic medical record.

2. The computer storage media of claim 1, wherein said first and second genetic test results are for one or more version of a particular gene.

3. The computer storage media of claim 1, further comprising:
   determining if the first and second genetic test results are different.

4. The computer storage media of claim 1, wherein the individual's genetic history is obtained from the individual's electronic medical record.

5. The computer storage media of claim 1, wherein the second genetic test result for the individual is received by querying a data structure for genetic test results compatible with the first genetic test result for the individual.

6. The computer storage media of claim 5, wherein querying a data structure includes matching identifiers from a controlled vocabulary.

7. The computer storage media of claim 1, further comprising recommending to a user that the second genetic test result be identified as the primary genetic test result based upon the determination that the technique used to generate the second genetic test result is a technique with higher resolution than the technique used to generate the first genetic test result.

8. The computer storage media of claim 1, wherein if the second genetic test result is identified as the primary genetic test result in the individual's genetic history, storing the first genetic test result as a supplemental result in the individual's genetic history.

9. One or more computer storage media having computer-executable instructions embodied thereon for performing a method for automatically correlating genetic test results for an individual, the method comprising:
   receiving a first genetic test result associated with the individual's genetic history, wherein the individual's genetic history is stored on one or more computer storage media associated with the individual's electronic medical record, said first genetic test result being identified as a primary genetic test result for the individual;
   receiving a second genetic test result for the individual;
   identifying a respective technique employed to determine each of said first and second genetic test results;
   determining whether the technique used to generate said first genetic test result and the technique used to generate said second genetic test result are the same;
   upon a determination that the technique used to generate said first test result is the same as the technique used to generate said second test result, storing said second test result as the primary genetic test result for the individual in the individual's electronic medical record;
   upon a determination that the technique used to generate said first test result is not the same as the technique used to generate said second test result, determining if the technique employed to generate said second genetic test result is of higher resolution compared to the technique employed to generate said first genetic test result and, upon determining that the technique employed to generate said second genetic test result is of higher resolution compared to the technique employed to generate said first genetic test result, storing said second genetic test result as said primary genetic test result and storing the first genetic test result as a supplemental test result in association with the individual's genetic history.

10. The computer storage media of claim 9, wherein the individual's genetic history is obtained from the individual's electronic medical record.

11. The computer storage media of claim 9, wherein the second genetic test result for the individual is received by querying a data structure for genetic test results compatible with the first genetic test result for the individual.

12. The computer storage media of claim 11, wherein querying a data structure includes matching identifiers from a controlled vocabulary.

13. The computer storage media of claim 9, further comprising recommending to a user that the second genetic test result be identified as the primary genetic test result.

14. A computer system embodied on one or more computer storage media having computer-executable instructions embodied thereon for automatically determining primary genetic test results for an individual, the system comprising:
   a first receiving module for receiving a first genetic test result associated with the individual's genetic history, wherein the individual's genetic history is stored in association with an electronic health record associated with the individual, said first genetic test result being identified as a primary genetic test result for the individual in the individual's electronic medical record;
   a second receiving module for receiving a second genetic test result for the individual;
   a ranking module for ranking the first and second genetic test results according to the resolution of each respective technique used to generate the first and second genetic test results;
   a determining module for determining, based on the ranking of the resolution of the respective techniques used to generate each of the first and second test results, if the second genetic test result should be identified as the primary genetic test result for the individual and, if so, identifying the second genetic test result as said primary genetic test result in the individual's electronic medical record; and
   a storing module for storing the second genetic test result as the primary genetic test result and the first genetic test result as a supplemental test result in association with the individual's genetic history.

15. The computer system of claim 14, further comprising a recommending module for recommending to a user that the second genetic test result be identified as the primary genetic test result.

* * * * *